US009505714B2

(12) United States Patent
Periana et al.

(10) Patent No.: US 9,505,714 B2
(45) Date of Patent: Nov. 29, 2016

(54) CONVERSION OF ALKANES TO ORGANOSELENIUMS AND ORGANOTELLURIUMS

(71) Applicant: The Scripps Research Institute, La Jolla, CA (US)

(72) Inventors: Roy A. Periana, Jupiter, FL (US); Michael M. Konnick, Palm Beach Gardens, FL (US); Brian G. Hashiguchi, Palm Beach Gardens, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/910,275

(22) PCT Filed: Aug. 6, 2014

(86) PCT No.: PCT/US2014/049903
§ 371 (c)(1),
(2) Date: Feb. 5, 2016

(87) PCT Pub. No.: WO2015/021126
PCT Pub. Date: Feb. 12, 2015

(65) Prior Publication Data
US 2016/0176812 A1    Jun. 23, 2016

Related U.S. Application Data

(60) Provisional application No. 61/862,732, filed on Aug. 6, 2013.

(51) Int. Cl.
| | | |
|---|---|---|
| *C07C 45/00* | (2006.01) |
| *C07C 395/00* | (2006.01) |
| *C07C 1/00* | (2006.01) |
| *C07C 209/00* | (2006.01) |
| *C07C 319/00* | (2006.01) |
| *C07F 7/00* | (2006.01) |
| *C07C 391/00* | (2006.01) |
| *C07C 1/32* | (2006.01) |
| *C07C 319/02* | (2006.01) |
| *C07C 319/14* | (2006.01) |
| *C07C 17/093* | (2006.01) |
| *C07B 39/00* | (2006.01) |
| *C07B 41/06* | (2006.01) |
| *C07B 43/04* | (2006.01) |
| *C07B 45/00* | (2006.01) |
| *C07B 47/00* | (2006.01) |
| *C07C 209/22* | (2006.01) |
| *C07C 231/10* | (2006.01) |
| *C07F 7/22* | (2006.01) |
| *C07F 9/50* | (2006.01) |

(52) U.S. Cl.
CPC ............ *C07C 395/00* (2013.01); *C07B 39/00* (2013.01); *C07B 41/06* (2013.01); *C07B 43/04* (2013.01); *C07B 45/00* (2013.01); *C07B 47/00* (2013.01); *C07C 1/321* (2013.01); *C07C 17/093* (2013.01); *C07C 45/00* (2013.01); *C07C 209/22* (2013.01); *C07C 231/10* (2013.01); *C07C 319/02* (2013.01); *C07C 319/14* (2013.01); *C07C 391/00* (2013.01); *C07F 7/2208* (2013.01); *C07F 9/5004* (2013.01)

(58) Field of Classification Search
CPC ..... C07C 45/00; C07C 395/00; C07C 1/321; C07C 209/22; C07C 319/02; C07F 7/00
USPC ........ 556/87; 562/899; 564/215, 463; 568/8, 568/69; 585/633
See application file for complete search history.

(56) References Cited

U.S. PATENT DOCUMENTS

| | | | |
|---|---|---|---|
| 5,166,428 A | 11/1992 | Cole-Hamilton et al. |
| 5,312,983 A | 5/1994 | Brown et al. |
| 6,077,714 A | 6/2000 | Spallholz et al. |
| 6,232,255 B1 | 5/2001 | Winslow et al. |
| 6,919,472 B2 | 7/2005 | Hazin et al. |
| 7,229,946 B2 | 6/2007 | Hazin et al. |
| 2002/0128161 A1 | 9/2002 | Wickham et al. |

(Continued)

FOREIGN PATENT DOCUMENTS

| | | |
|---|---|---|
| CN | 101591220 | 12/2009 |
| CN | 101591220 A1 * | 12/2009 |

(Continued)

OTHER PUBLICATIONS

Krief et al., "Synthesis of Diselenides and Selenides from Elemental Selenium" Tetrahedron Letters, (Feb. 2002) pp. 3083-3086.
United States Patent and Trademark Office, International Search Report and Written Opinion for International PCT Application No. PCT/US2014/049903, 9 pgs (Oct. 30, 2014).
Dransfield et al., "Studies on Biological Methylation. Part XV. The Formation of Dimethyl Selenide in Mould Cultures in Presence of D- and L-Methionine, or of Thetins, All containing the $^{14}CH_3$ Group," Journal of the Chemical Society, 1153-1160 (1955).

(Continued)

Primary Examiner — Sikarl Witherspoon
(74) Attorney, Agent, or Firm — Leydig, Voit & Mayer, Ltd.

(57) ABSTRACT

The invention provides processes and materials for the efficient and costeffective functionalization of alkanes and heteroalkanes, comprising contacting the alkane or heteroalkane and a soft oxidizing electrophile comprising Se(VI) or Te(VI), in an acidic medium, optionally further comprising an aprotic medium, which can be carried out at a temperature of less than 300 C. Isolation of the alkylselenium or alkyltellurium intermediate allows the subsequent conversion to products not necessarily compatible with the initial reaction conditions, such as amines, stannanes, organosulfur compounds, acyls, halocarbons, and olefins.

21 Claims, 5 Drawing Sheets

(56) References Cited

U.S. PATENT DOCUMENTS

| | | |
|---|---|---|
| 2004/0198042 A1 | 10/2004 | Shenai-Khatkhate |
| 2006/0241327 A1 | 10/2006 | Periana et al. |
| 2008/0004366 A1 | 1/2008 | Yamago et al. |
| 2008/0009597 A1 | 1/2008 | Yamago et al. |
| 2009/0264688 A1 | 10/2009 | Periana et al. |
| 2009/0326313 A1 | 12/2009 | Nakamura et al. |
| 2010/0158967 A1 | 6/2010 | Reid et al. |
| 2011/0301235 A1 | 12/2011 | Erlanson et al. |
| 2013/0165595 A1 | 6/2013 | Reid et al. |

FOREIGN PATENT DOCUMENTS

| | | |
|---|---|---|
| WO | WO 92/06758 A | 4/1992 |
| WO | WO 2005/039553 A1 | 5/2005 |
| WO | WO 2006/063606 A1 | 6/2006 |
| WO | WO 2011/160060 A2 | 12/2011 |
| WO | WO 2013/104605 A2 | 7/2013 |

OTHER PUBLICATIONS

Hashiguchi et al., "Designing Catalysts for Functionalization of Unactivated C-H Bonds Based on the CH Activation Reaction," *Accounts of Chemical Research*, 45(6): 885-898 (Jun. 2012).

European Patent Office, Extended European Search Report in European Patent Application No. 14833997.1 (Jun. 23, 2016).

\* cited by examiner

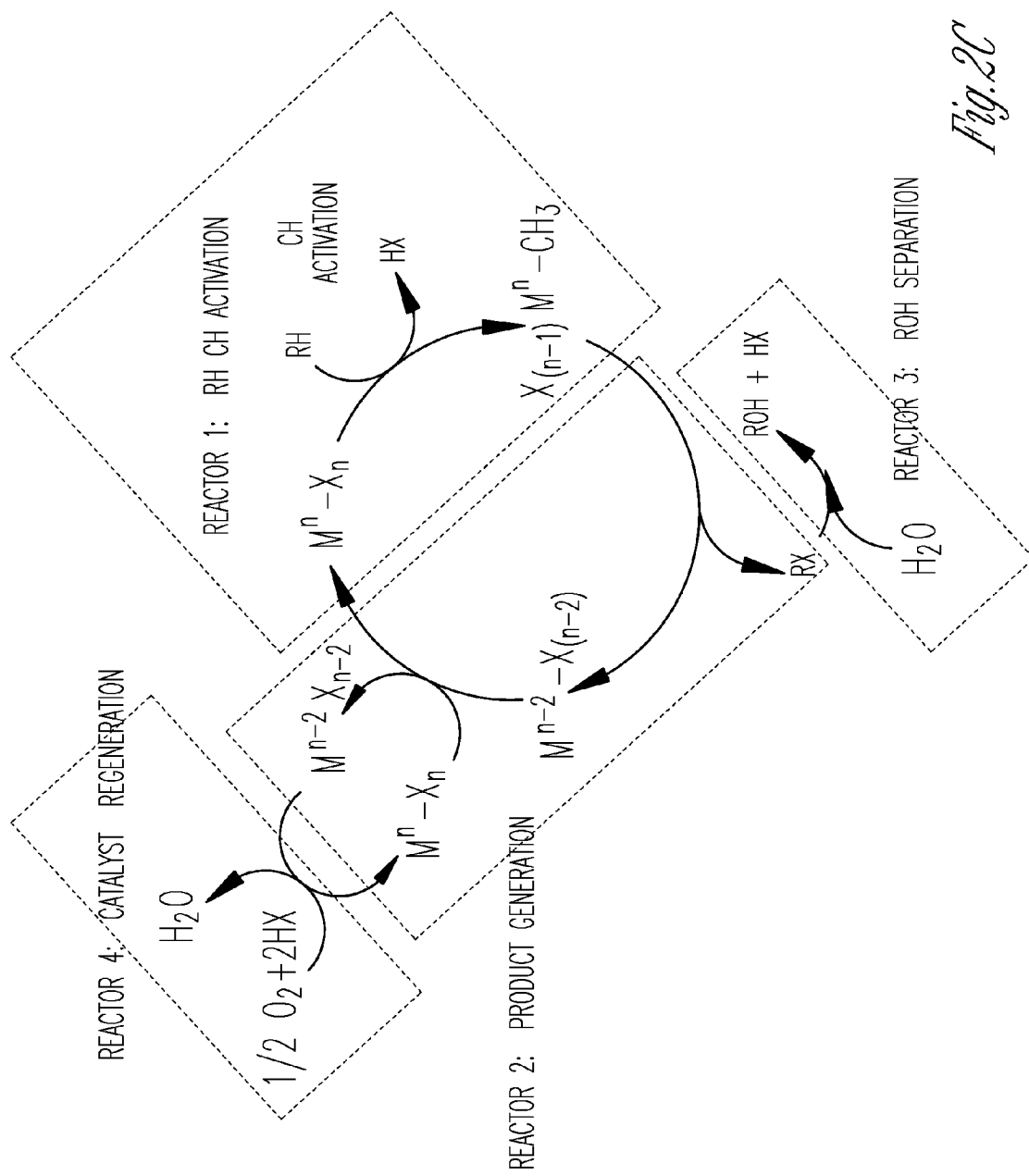

CONVERSION OF ALKANES TO ORGANOSELENIUMS AND ORGANOTELLURIUMS

CROSS-REFERENCE TO RELATED APPLICATIONS

This application is a U.S. national phase of International Patent Application No. PCT/US2014/049903, filed Aug. 6, 2014, which claims the benefit of U.S. Provisional Application No. 61/862,732, filed Aug. 6, 2013, the disclosure of which is incorporated herein by reference in its entirety.

STATEMENT OF GOVERNMENT SUPPORT

This invention was made with government support under grant number GQ10044-133945, by the U.S. Department of Energy. The government has certain rights in the invention.

BACKGROUND

Alkanes are an abundant but chemically intractable class of compounds that offer the potential of inexpensive substrates for conversion to functionalized chemical products, provided that economical processes can be developed to convert the alkanes to substances containing functional groups such as alcohols, amines, acyls, olefins, halocarbons, organosulfur compounds and organotin compounds.

Natural gas (NG) is becoming an increasingly abundant resource in the US and around the world. While NG is used for heating it would be ideal to upgrade this resource to chemicals and liquid fuels. This could augment or potentially replace petroleum as the feedstock for chemicals and fuels. Natural gas is also abundantly available in remote locations where transportation to centers of use is not economically viable. In these cases it would be desirable to have an inexpensive process to convert the natural gas to a more easily transported form such as a liquid. However, the existing high-temperature, indirect processes based on the conversion of natural gas to syngas ($CO/H_2$) followed by conversion of the syngas to chemicals and liquid fuels are too energy and capital intensive to economically compete with products from petroleum. Current processes for the conversion of natural gas to fuels and chemicals require high-temperature (>800° C.) to generate synthesis gas or olefins. FIG. 1(A), below, illustrates some of these reactions of alkanes. These processes are very capital and energy intensive and are only economical at very large scales. It is generally considered that a direct, lower temperature (<300° C.), selective process to convert the gases in NG (primarily methane, ethane and propane) to liquid products such as alcohols could be used to generate chemicals and liquid fuels at much lower cost than the existing high-temperature, indirect syngas processes.

A technology for the direct low-cost conversion of the major components of natural gas (methane, ethane, propane) to liquid fuels and chemicals such as oxygenates would provide a path to increased value for these sources of natural gas. The potential market for such technology is large; e.g, the global market value for ethylene glycol is over $20 billion/yr with the US at over $4 billion/yr. The markets for other oxygenates such as methanol, ethanol (that can also be inexpensively converted to ethylene and polyethylene), isopropanol, propylene glycol, etc., are also very large. The liquid fuels market is enormous; a 2% penetration of the projected US transportation fuels market, equivalent to the projected annual growth rate in the US, would represent about 50 plants of 14,500 barrel per day capacity.

Other hydrocarbon sources are available for which it may also be desirable to carry out one or more of the functionalization reactions described herein. For example, crude or refined petroleum products, tar sand extracts and distillates, coal and coal liquification products, and other materials containing alkane-like moieties, can be substrates for the reactions described herein, for the production of valuable industrial chemicals.

SUMMARY

The invention is directed to the use of inventive compositions and systems in carrying out an economically viable process for the production of organoselenium and organotellurium compounds from alkanes or heteroalkanes. Alkanes useful as substrates in the methods of the invention include low molecular weight natural gas alkanes such as methane, ethane, and propane. The organoselenium and organotellurium intermediates can also be prepared by the methods herein from higher molecular weight alkanes, such as petroleum and coal-derived products. Organoselenium and organotellurium products can also be produced from heteroalkanes, that is, alkanes having chemical groups comprising heteroatoms such as nitrogen, oxygen, and halogens as substituents, or otherwise incorporated into the alkane structure. The reaction products of the substrate alkanes, referred to herein as alkylselenium (organoselenium) or alkyltellurium (organotellurium) intermediates, can be used in the subsequent preparation of a variety of chemical derivatives of the alkanes or heteroalkanes.

For example, the isolated alkylselenium or alkyltellurium compounds can undergo oxidation, e.g., with hydrogen peroxide or the like, to yield alkanols (carbinols), or, e.g., with hydrazine to yield amines. The alkylselenium or alkyltellurium compounds can also be converted, using known chemistry, to organotin intermediates (stannanes), to phosphines, to organosulfur compounds, to halocarbons, and other functionalized alkanes, by reaction of the alkylselenium or alkyltellurium compound with the appropriate reagents. The alkylselenium or alkyltellurium compound can also undergo carbonylation reactions, yielding acyl compounds from the corresponding alkane, such as aldehydes, carboxylic acids, amides, esters and the like. The alkylselenium or alkyltellurium products can further undergo elimination reactions, producing alkene products from the alkane substrates.

The alkylselenium or alkyltellurium compound can be reacted in situ, or can be isolated for subsequent chemical transformation. The ability to isolate the intermediate of the alkane reaction products produced by the methods herein allows chemical reactions to be carried out that would otherwise be incompatible with the alkane functionalization reaction.

The abundant hydrocarbon, natural gas, can be used as a source of the alkanes, and thus can serve as a cost-effective feedstock for the production of organic chemicals, lubricants, and fuels from this source. Other hydrocarbon sources, such as petroleum and petroleum distillates, tar sand and shale oil materials, coal and processed coal products, biomass resources and the like, can also be used as substrates for practice of the inventive methods described and claimed herein. Heteroalkanes, such as carbinols, halocarbons, and other organic compounds comprising an $sp^3$-hybridized carbon atom bearing at least one hydrogen atom, can also be substrates for reactions of the invention.

The inventive processes can allow for production of the organoselenium- or organotellurium-functionalized alkanes and heteroalkanes in high yield and with high volumetric productivity, in the absence of oxygen or hydrogen peroxide. Inexpensive oxidants are used that can be regenerated with oxygen or other readily available oxidants such as hydrogen peroxide in a separate process or reactor. The organo selenium or organotellurium products can be further converted to a wide range of useful products, including amines, organosulfur compounds, organotin compounds, halocarbons, acyl compounds, olefins, and the like.

In various embodiments, the invention provides a process for the conversion of an alkane or a heteroalkane, wherein the alkane or heteroalkane comprises at least one $sp^3$-hybridized carbon atom, to a corresponding alkylselenium or alkyltellurium compound resulting from a C—H bond activation reaction involving an $sp^3$-hybridized carbon atom, comprising (a) contacting the alkane or heteroalkane and a soft oxidizing electrophile comprising Se(VI) or Te(VI), in an acidic medium, optionally further comprising an aprotic medium; then, (b) separating the respective alkylselenium or alkyltellurium product.

The process can further comprise a step of regeneration of the soft oxidizing electrophile by contacting the Se or Te-containing reaction product of the soft oxidizing electrophile and the alkane or heteroalkane with an oxidant.

The alkylselenium or alkyltellurium compounds obtained by this process can undergo further reactions to provide functionalized alkane or heteroalkane products, e.g., they can be oxidized/hydrolyzed to yield the corresponding alkanol, or can undergo other reactions not compatible with the reaction conditions used for the initial step of alkane functionalization by C—H bond activation, e.g., to yield amines by reaction with hydrazine or other nitrogen-containing reagents.

Other products can be obtained from the alkylselenium or alkyltellurium compounds, such as products of stannylation, thiolation, phosphinylation, carbonylation, elimination, or halogenation reactions.

DETAILED DESCRIPTION

Figure 1:
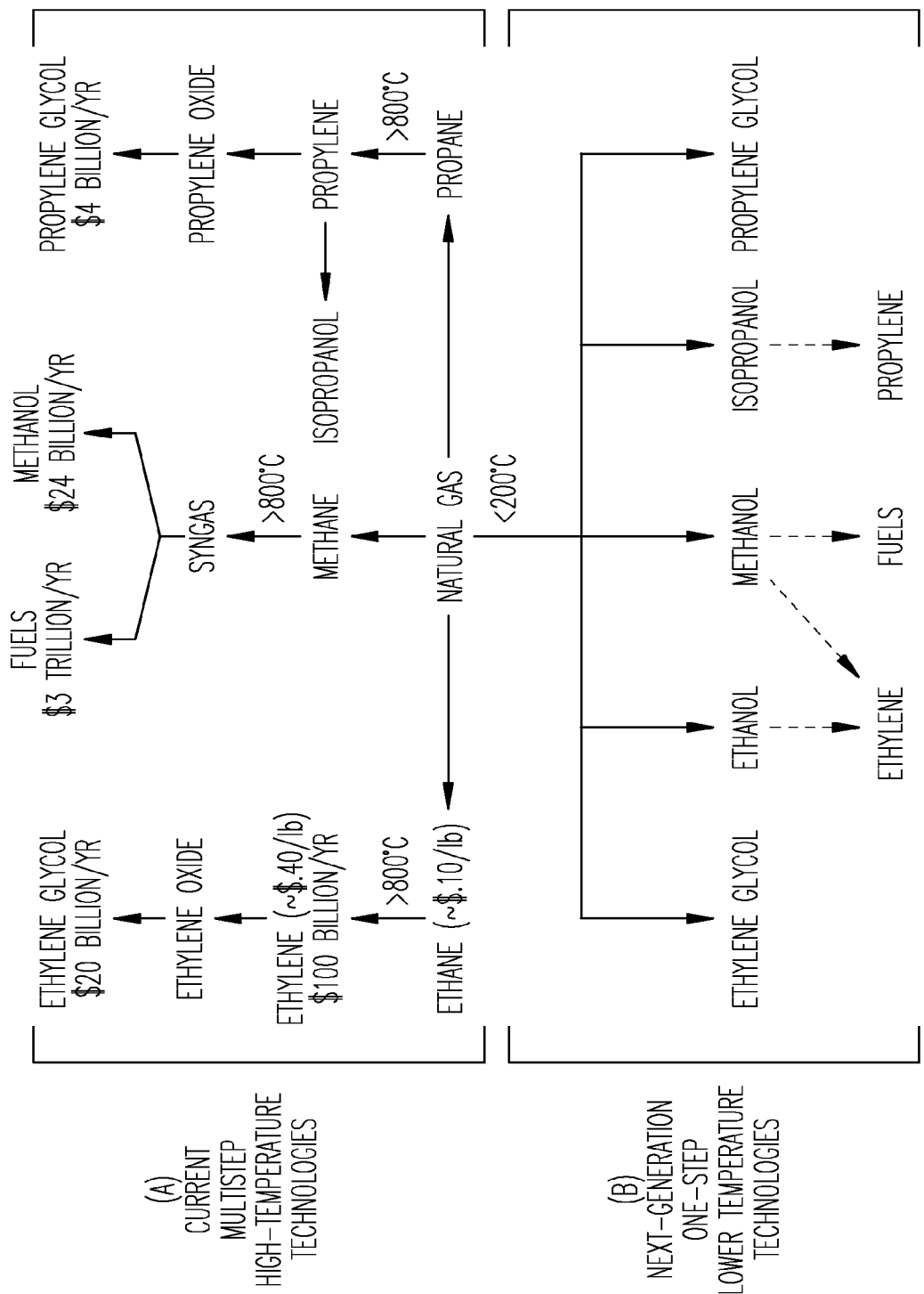
FIG. 1 is a schematic showing conversion of alkanes, such as natural gas alkanes, to functionalized alkane products: (A) lines indicate conversions accessible using prior art methods, and (B) lines indicate conversions that can be carried out using processes of the present invention.

This invention provides, in various embodiments, processes encompassing the use of novel reagents that facilitate the conversion of alkanes and heteroalkanes directly, selectively and in high yields and volumetric productivity, to the corresponding alkylseleniums and alkyltelluriums at temperatures below 300° C., such as in liquid phase batch reactors. The overall reaction is the functionalization of the alkane or heteroalkane substrate with a soft oxidizing electrophile comprising Se(VI) or Te(VI), in an acidic medium comprising trifluoroacetic acid, to provide respectively an alkylselenium or alkyltellurium reaction product. A hydrogen atom disposed on an $sp^3$-hybridized carbon atom is replaced by a selenium or tellurium atom, which can bear other substituents as well. When the substrate is an alkane, the product is the corresponding alkylselenium or alkyltellurium. When the substrate is a heteroalkane, the product is the corresponding organoselenium or organotellurium derivative of the heteroalkane, where a hydrogen atom disposed on an $sp^3$-hybridized carbon atom is replaced by a selenium or tellurium atom, which can bear other substituents as well.

The alkylselenium or alkyltellurium compounds can then be converted to other materials. The reagents can be regenerated to active form by the use of atmospheric oxygen or other oxidants. The reactions can optionally be carried out in the absence of a superacid. In various embodiments, the presence of a superacid, e.g., $CF_3SO_3H$, is not required to carry out a method of the invention. The reaction of the selenium or tellurium atom in an oxidized state with the C—H bond, followed by conversion of the selenium- or tellurium-containing organic product to a downstream product can release the selenium or tellurium in reduced form, from which the oxidized, reactive form of the selenium or tellurium can be regenerated, which can provide a sustainable process with little or no selenium or tellurium waste byproduct formed.

An alkane, as the term is used herein, refers to compound having a chemical structure that includes at least one $sp^3$-hybridized carbon atom, bearing at least one hydrogen atom. The reactions described and claimed herein involve the activation of the C—H bond of an $sp^3$-hybridized carbon atom to provide an alkylselenium or alkyltellurium reaction product. Thus, the term embraces simple lower alkanes such as natural gas components methane, ethane, propane, butane, isobutane, and the like; also, higher molecular weight carbon structures such as those derived from petroleum, coal, tars, biomass, and the like, which may have molecular weights ranging into the hundreds of daltons, or higher. A substrate of the present reaction is a molecule that includes at least one $sp^3$-hybridized carbon atom, wherein at least one substituent of that carbon atom is a hydrogen atom such that a C—H bond is present. A related type of substrate for a reaction involving activation of the C—H bond of the $sp^3$-hybridized carbon atom is a "heteroalkane", by which is meant a compound comprising at least one $sp^3$-hybridized carbon atom bearing a hydrogen atom, wherein the heteroalkane compound in addition comprises at least one "heteroatom", i.e., a non-carbon/non-hydrogen atom. Examples of heteroatoms include atoms of elements such as oxygen, nitrogen, a halogen such as chlorine, a metal such as tin, or the like. Thus, an heteroalkane substrate as the term is used herein can be an alkylcarbinol, alkylamine, halocarbon, organometallic compound, or the like. Examples of heteroalkane substrates useful for practice of a method of the invention include alcohols such a n-propanol or n-butanol, compounds comprising an ether oxygen or an ester/amide group, and the like. For instance, a method of the invention can be used to provide organo selenium/organotellurium reaction products of unsubstituted alkane substrates such as butane, and can also be used to provide analogous reaction products of heteroalkanes such as butanol, halobutanes, butanoyl compounds such as esters and amides, and the like.

Some key advantages to the present invention in its various embodiments are avoiding the high temperature, multistep, complex and capital intensive processes that are currently use for the conversion of alkanes to functional products such as olefins, diesel or methanol. Examples of these advantages are illustrated in the scheme shown in FIG. 1. FIG. 1(A) shows existing processes for conversions of simple alkanes. As shown in FIG. 1(B), the invention described in this disclosure would allow new, more direct processes for the conversion of the alkanes to other products when compared to the existing processes, FIG. 1(B); FIG. 1(A) shows art processes for comparison. Capital and operating costs are in many cases the major contribution to the production costs for these large volume materials. Reducing the number of steps, temperatures, heat management and reactor cost would substantially reduce these costs as well as overall energy consumption, while increasing atom efficiencies for the generation of the species from alkane-rich feedstocks such as natural gas. The isolation of the alkylselenium or alkyltellurium intermediates allows the production of a wide variety of final products therefrom.

An outstanding feature of various embodiments of the soft oxidizing electrophiles useful in carrying out the methods of the present invention are that they are based on inexpensive main group elements such as selenium or tellurium and can convert each alkane or heteroalkane to a corresponding functionalized alkane or heteroalkane separately or as part of a mixture. Significantly, these direct conversions avoid the high temperature and resulting large capital investment required by current indirect processes that proceed by generation of syngas or olefinic intermediates. The discovery of these catalyst/reagent designs builds on new alkane C—H activation chemistry developed over the last 20 years, that enables the cleavage of C—H bond without the generation of the free radicals involved in oxidation technologies presently used in the industry.

These novel process designs can be the basis for proprietary platform technologies resulting in the lowest cost commercial processes for the conversion of natural gas to chemicals, liquid fuels and lubricants. This will make possible monetization of associated and stranded gas as well as substantially increasing the market and value for the extensive natural gas reserves throughout the US and the world. The technology as disclosed and claimed in the present patent application can, for example, allow natural gas to be used to augment and potentially displace the use of petroleum as a feedstock.

While the soft oxidizing electrophile is itself reduced in the reaction with the alkane or heteroalkane, it can be readily regenerated with oxygen, hydrogen peroxide etc., such as in a continuous, repetitive consecutive process or a parallel process. In the reaction scheme shown below, the product of Reactor 2, i.e., the alkylselenium or alkyltellurium, are formed with a stoichiometric incorporation of the soft oxidizing selenium or tellurium reagent, but upon subsequent hydrolysis as shown for Reactor 3, or in another chemical conversion of the alkylselenium or alkyltellurium reaction product, the byproduct incorporating selenium or tellurium resulting from the hydrolysis or other conversion reaction of Reactor 3 can be captured and recycled, e.g., by oxidation, and returned to the overall process.

The overall reaction can be represented by the reaction sequence wherein the net reaction amounts to a low-temperature, selective, and direct oxidation of the alkane or heteroalkane with molecular oxygen to yield an alcohol in a multistep, multi-reactor, process.

Scheme 1:

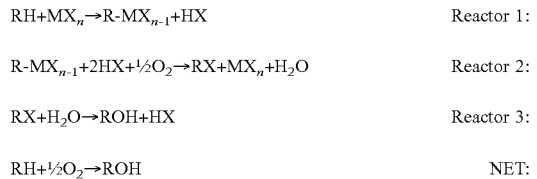

Figure 2A:
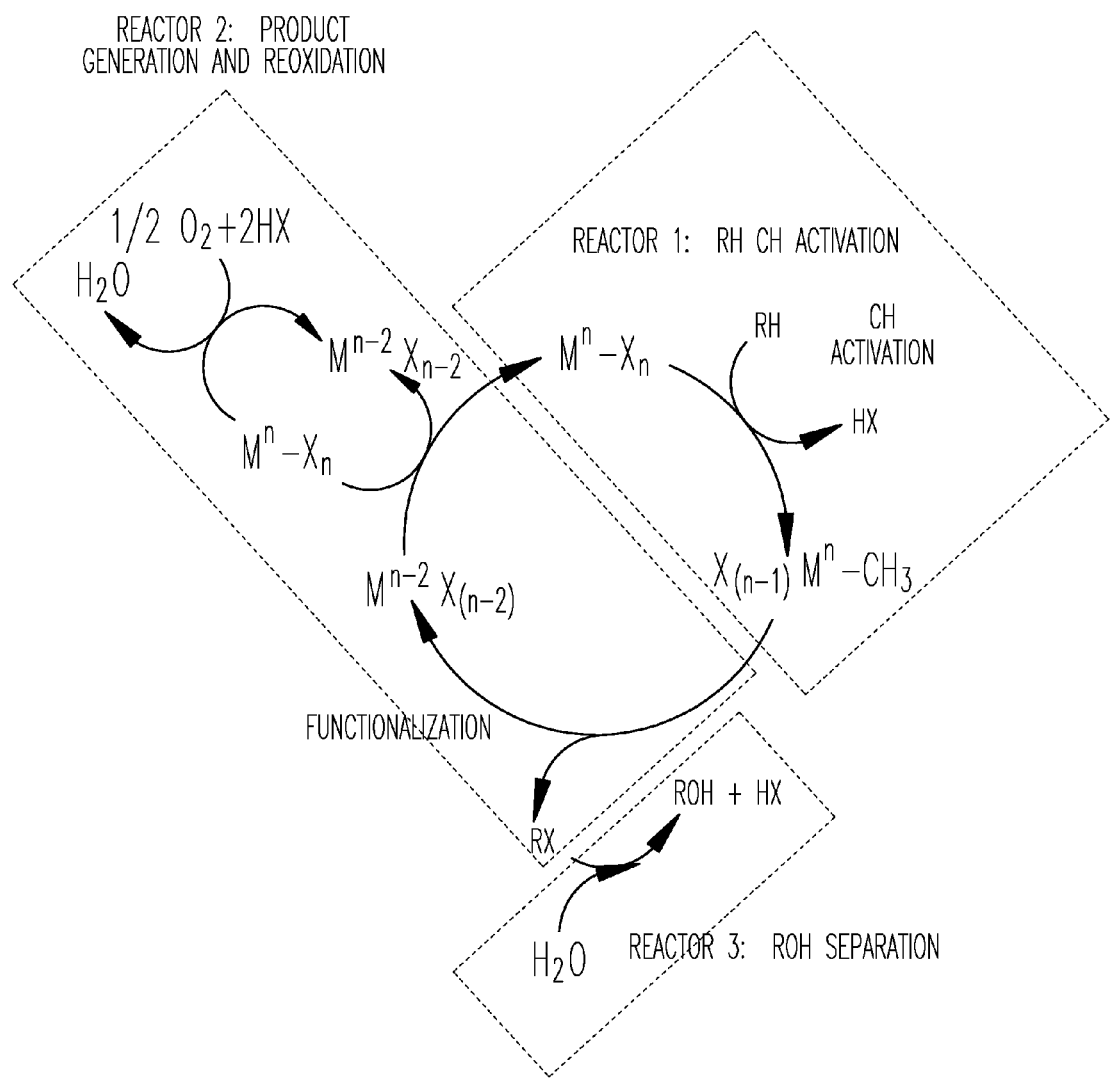
FIGS. 2 (A), (B), and (C) depict reaction schemes showing a cycle of reactions whereby a process of the invention can be used to accomplish an overall conversion of an alkane to an alkyltellurium or alkylselenium compound.
Figure 2B:
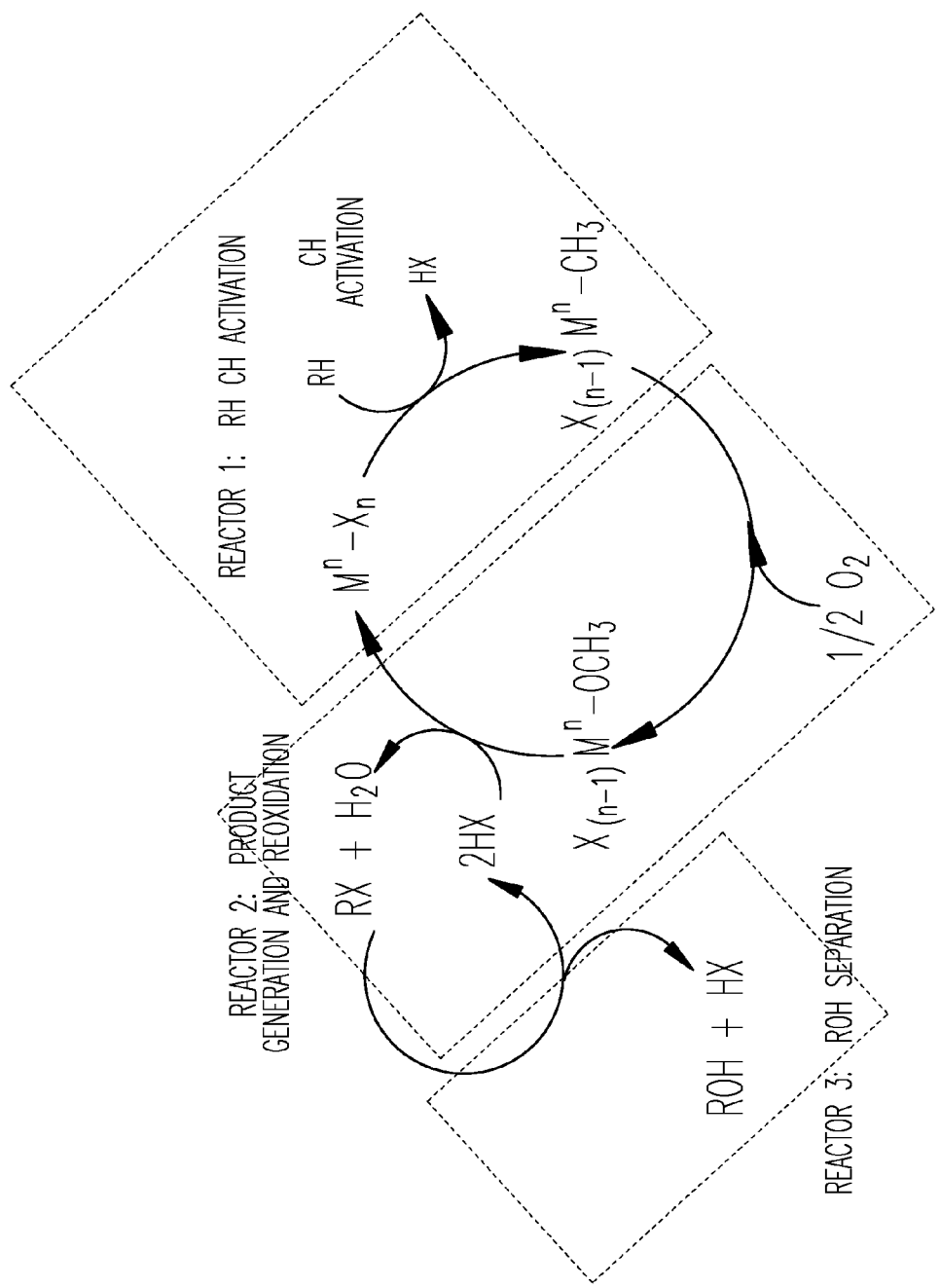

As shown in FIGS. 2(A) and 2(B), illustrating the execution of Scheme 1 in a multi-reactor setup, the C—H activation reaction is carried out to generate $R\text{-}MX_{n-1}$ in a stoichiometric reaction between RH and $MX_n$. Thus, $R\text{-}MX_{n-1}$ is the product generated in Reactor 1. The stoichiometric generation of $R\text{-}MX_{n-1}$ in Reactor 1, Scheme 1 can be advantageous as this could allow the $R\text{-}MX_{n-1}$ to the functionalized under conditions that are not compatible with the C—H activation reaction, as discussed below. The alkylselenium or alkyltellurium reaction product produced in Reactor 1 can then be isolated for subsequent conversion to other compounds.

In Scheme 1, the reaction takes place in an acidic medium, optionally further comprising an aprotic solvent such as liquid sulfur dioxide, trifluoroethanol, tetrachloroethane, or dichloromethane, or a mixture thereof. In various embodiments, the acid medium in which the C—H bond activation reaction occurs is free of a superacid, e.g., is free of a superacid such as $CF_3SO_3H$ or other superacid compound of comparably high acidity.

In FIG. 2(C), a reaction scheme according to Scheme 2 is depicted:

Scheme 2:

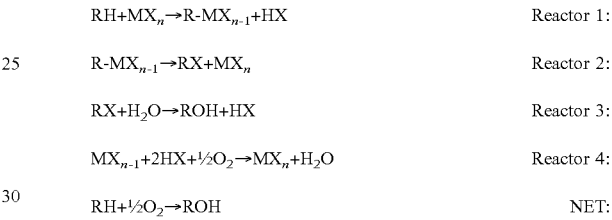

In Scheme 2, regeneration of the MXn species, e.g., the Se(VI) or Te(VI) reagent, takes place in a separate Reactor 4, as shown in FIG. 2(C).

Figure 3:
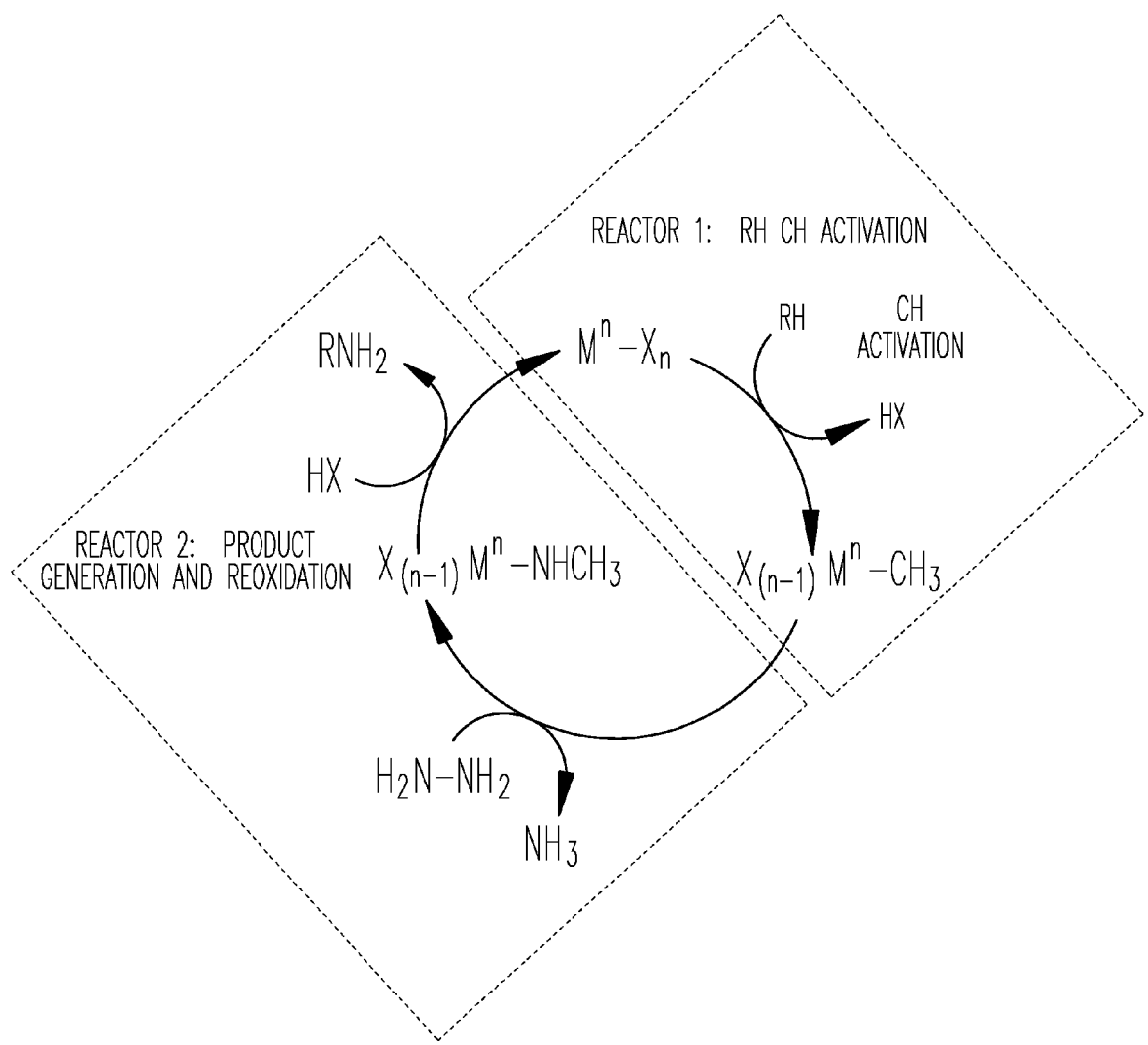
FIG. 3 depicts a reaction scheme for production of amines according to the present invention.

An advantage of isolating the alkylselenium or alkyltellurium intermediate is that subsequent reactions can be carried out that would not reasonably be expected to occur under the reaction conditions used for hydrolysis of the alkylselenium or alkyltellurium intermediate to yield alkanols, such as reaction with hydrazine to generate amine products (see FIG. 3). Scheme 3 illustrates this conversion:

Scheme 3:

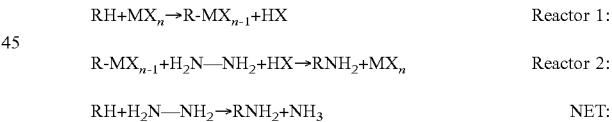

In these exemplary schemes, the regenerable stoichiometric oxidant $M^nX_n$ (also termed $MX_n$) is understood to be an electrophilic cation at the oxidation state equal to n, a soft oxidizing electrophile as defined below, which undergoes stoichiometric reaction with the alkane to yield a functionalized alkane RX, e.g., the alkylselenium or alkyltellurium reaction product, in the reaction of Reactor 1 of Scheme 1, 2, and 3, above. In the present invention, it is understood that M refers to a non-metallic element such as selenium (Se) or tellurium (Te).

In this reaction, X can be an anion comprising an electron withdrawing group, e.g., the conjugate base of an acid; e.g., $CF_3CO_2^-$, $HOSO_2O^-$, $CH_3SO_2O^-$, $CF_3SO_2O^-$, $CH_3CO_2^-$, or can be an O or OH group. Electron withdrawing groups can be utilized in this reaction in order to prevent further reaction (i.e., over-oxidation) the alcohol, ROH, or other functionalized alkane or heteroalkane, RX, from further reaction with electrophilic species $MX_n$. This blocking of subsequent reaction of the alcohol or other monofunctionalized alkane and the electrophile results from the generation of positive charge on the carbon in the reaction of the C—H bond with the electrophilic cation, $M^{n+}$. Over-oxidation of methane functionalization products under reaction conditions is a undesired side reaction in many methane functionalization processes, which can result in production of the useless carbon dioxide and unnecessary consumption of the electrophilic species.

In the first reaction, taking place in Reactor 1 as shown in Schemes 1 and 2, the reaction is stoichiometric, and oxidative regeneration of the electrophile reduction product to the soft oxidizing electrophile takes place in a separate reactor.

In a subsequent reaction in separate Reactor 2 as shown in Scheme 1, the reduction product of the soft oxidizing electrophile, $M^{(n-2)}X_{n-2}$, can undergo reaction with an inexpensive oxidizing regeneration species such as $O_2$ or $H_2O_2$ to regenerate the soft oxidizing electrophile species $M^nX_n$, in condition for further reaction with the alkane or heteroalkane RH. It is also recognized that the oxidation state of the reduced electrophilic species can be (n−1). In this case equation 1 would be replaced by the reaction stoichiometry of $RH+2M^nX_n \rightarrow RX+2M^{(n-1)}X_{n-1}+HX$.

In the reaction of Reactor 3 of Schemes 1 and 2 above, the functionalized alkane or heteroalkane can undergo a hydrolysis reaction with water under suitable conditions to yield the alcohol, ROH, corresponding to the starting alkane or heteroalkane, RH. The anion X from the $MX_n$ species is also recovered at this stage. The net reaction is thus oxidation of the alkane or heteroalkane to the corresponding alcohol, e.g., methane to methanol. In the analogous reaction occurring in Reactor 2 of Scheme 3, the alkylselenium or alkyltellurium reaction product can undergo a reaction with hydrazine, $H_2NNNH_2$, to yield an amine product. Other reactions of the primary alkylselenium or alkyltellurium reaction product are discussed below.

An example of $MX_n$ is $Te(OH)_6$ where M=Te and X=OH. This salt has been shown to catalytically react rapidly with various alkanes and heteroalkanes, RH, in $CF_3CO_2H$ to generate the corresponding organotellurium product. While the species $MX_n$ is referred to herein as a "salt", it is understood that there may be a significant amount of covalent bonding between the M atoms and the X moieties, depending upon the exact identify of the $MX_n$ material used. In the embodiments using selenium or tellurium, the species $MX_n$ likely has very considerable covalent character.

We believe it will be possible to regenerate this catalyst using oxidants other than $H_2O_2$ such a chlorine, elemental oxygen, and the like, as well as electrochemically oxidizing the reduced Se and Te species back to their reactive the Se(VI) and Te(VI) oxidation states, by applying an oxidative electrochemical potential to the electrophile reduction product.

In various embodiments, the invention is directed to processes involving the utilization of selenium and tellurium in high oxidation states, including but not limited to $Te(OH)_6$ and $H_2SeO_4$, to affect the selective conversion of primary feedstock hydrocarbons including, but not limited to, methane, ethane, propane, and benzene, to functionalized alkane products such as methylated selenium and tellurium intermediates (see Table 1, examples 12 and 13, below). A key aspect of this invention is the utilization of weak acid media (such as trifluoroacetic acid) to both facilitate reactivity and deactivate the partially oxidized products towards further oxidation. Similar reaction conditions can be used to convert heteroalkanes, e.g., carbinols, to their corresponding selenium and tellurium intermediates.

This invention includes the use of novel reagents and catalysts that facilitate the conversion of the alkanes directly, selectively and in high yields and volumetric productivity to the corresponding alcohols at temperatures below 250° C. in liquid phase batch reactors. The specific species, tellurium and selenium reagents, are also relatively non-toxic as compared to other post transition elements (thallium, lead) which are capable of affecting similar reactivity.

The key advantages to these reactions is avoiding the high temperature, multistep, complex and capital-intensive processes that are currently use for the conversion of alkanes to functional products such as olefins, diesel or methanol. Examples of these advantages are illustrated in FIG. 1. As shown in this scheme the invention described in this disclosure would allow new, more direct processes (shown in dotted lines) for the conversion of the alkanes to alcohol products when compared to the existing processes (shown in solid lines). Capital and operating costs are in many cases the major contribution to the production costs for these large volume materials. Reducing the number of steps and the temperatures would substantially reduce these costs as well as overall energy and atom efficiencies for the generation of the species from alkanes feedstocks in natural gas.

We have established the ability of Se and Te reagents to effect selective CH functionalizations on methane, ethane, propane and benzene to form isolable alkylselenium or alkyltellurium compounds.

According, in various embodiments, the invention can provide a process for the conversion of an alkane or a heteroalkane, wherein the alkane or heteroalkane comprises at least one $sp^3$-hybridized carbon atom, to a corresponding alkylselenium or alkyltellurium compound resulting from a C—H bond activation reaction involving an $sp^3$-hybridized carbon atom, comprising (a) contacting the alkane or heteroalkane and a soft oxidizing electrophile comprising Se(VI) or Te(VI), in an acidic medium, optionally further comprising an aprotic medium; then, (b) separating the respective alkylselenium or alkyltellurium product.

For instance, the acidic medium can comprise trifluoracetic acid, acetic acid, or a mixture thereof.

The process can further comprise a step of regeneration of the soft oxidizing electrophile by contacting the Se or Te containing electrophile reduction product of the soft oxidizing electrophile and the alkane or heteroalkane with an oxidant under conditions suitable to regenerate the soft oxidizing electrophile comprising Se(VI) or Te(VI).

For example, an alkane undergoing oxidation, which can be obtained from natural gas, can be methane, ethane, or propane, or any mixture thereof.

In regeneration of the soft oxidizing electrophile from the electrophile reduction product, taking place in a separate reactor, the oxidant can comprise any of molecular oxygen, hydrogen peroxide, chlorine, nitric acid, or ozone. For example, the oxidant can consist essentially of hydrogen peroxide.

Alternatively, regeneration of the soft oxidizing electrophile can be achieved by application of an oxidizing electrochemical potential.

In various embodiments, the acidic medium consists essentially of trifluoroacetic acid. Or, the acidic medium consists essentially of acetic acid. Alternatively, the acidic medium can further comprise an aprotic medium, comprising an anhydrous, poorly nucleophilic, polar liquid; e.g., the aprotic medium can comprise liquid sulfur dioxide, trifluoroethanol, tetrachloroethane, or dichloromethane, or a mixture thereof.

Although not wishing to be bound by theory, it is believed by the inventors herein that the process claimed and disclosed herein proceeds via an organic species comprising the selenium or tellurium atom covalently bonded to a carbon atom of the alkane, to yield the functionalized alkylselenium or alkyltellurium reaction product and the electrophile reduction product.

In various embodiments, regeneration of the soft oxidizing electrophile species can take place by contacting with an oxidant, in a separate reactor, to provide regenerated soft oxidizing electrophile comprising Se(VI) or Te(VI). The oxidative regeneration of the soft oxidizing electrophile can be carried out in the presence of an oxidative regeneration catalyst. For example, the oxidative regeneration catalyst can comprise copper, silver, iron, or vanadium, as shown in the following scheme for the regeneration of Te(VI):

Scheme 4:

$$2CuX + \tfrac{1}{2}O_2 + 2HX \rightarrow 2CuX_2 + H_2O \quad (7)$$

$$2CuX_2 + Te(OH)_4 \rightarrow Te(OH)_6 + 2CuX \quad (8)$$

In this embodiment, oxygen serves as the ultimate oxidant, as the copper species is regenerated by oxygen, after re-oxidation of the Te(OH)$_4$ species to yield the soft oxidizing electrophile Te(OH)$_6$. Other elements can serve as catalysts for the reaction of the regenerating oxidant and the reduced electrophile, such as silver, iron, or vanadium. However, the regeneration of the soft oxidizing electrophile can be carried out using only an oxidant, e.g., oxygen, without any requirement for the presence of a catalyst.

In other embodiments, the oxidant can directly regenerate the soft oxidizing electophilic species without a catalyst.

In various embodiments, the soft oxidizing electrophile comprising Se(VI) or Te(VI), or the corresponding electrophile reduction product, or both, can be immobilized on a solid support contained within a reactor. For example, the soft oxidizing electrophile and the electrophile reduction product can be bound to a suitable organic resin such that the selenium or tellurium atom is retained in the reactor and not dissolved in the product stream as the reaction takes place.

The process can be carried out such that the alkane and soft oxidizing electrophile comprising Se(VI) or Te(VI) can be carried out in a two reactor circulating liquid phase system, wherein the reaction of the alkane and the soft oxidizing electrophile is carried out in a first reactor, and the oxidative regeneration of the separated electrophile reduction product is carried out in a second reactor. For example, the process in the first reactor and the process in the second reactor are carried out over time with a phase difference of half of one full cycle.

Table 1, above, provides examples of processes of oxidation of hydrocarbons methane and ethane, using soft oxidizing electrophilic reagents Te(OH)$_6$, and H$_2$SeO$_4$, under the conditions shown.

The chemistry accomplished by the processes disclosed and claimed herein are among the most difficult to carry out with high efficiency and selectivity. Alkanes are referred to as "paraffins", i.e., lacking affinity or reactivity, with good reason. Conversion of the C—H bond of alkanes such as methane, ethane, and propane is however essential to the use of this abundant hydrocarbon feedstock in a rational way. Chemical modification of higher alkanes, such as those obtained from crude oil, tar sands, shale oil, and coal, can provide products useful as organic intermediates and materials. Modifications of heteroalkanes can also provide valuable industrial synthetic intermediates and products, such as acyls, olefins, stannanes, amines, and the like. The presently disclosed processes represent a significant improvement in the technology available to carry out such reactions and economically provide useful fuels, lubricants, and other synthetic organic compounds such as polymers and solvents.

The alkane or heteroalkane, comprising at least one sp$^3$-hydridized (tetrahedral) carbon atom, is functionalized by C—H bond activation of the selenium or tellurium atom in the process as described above. The alkylselenium or alkyltellurium reaction product is sufficiently stable to allow isolation, such as by extraction from the reaction milieu, e.g., by a liquid-liquid extraction procedure.

The alkylselenium or alkyltellurium reaction product, for example in the form of a solution in an organic solvent from a liquid-liquid extraction process, can then be converted into a variety of products, as described herein, under suitable conditions. The reaction can be carried out in a separate reactor, thus isolating the secondary reaction from the reagents present in the initial functionalization reactor. At this stage, the selenium or tellurium byproduct can be recovered and recycled in an oxidative process, as described above, to regenerate the selenium or tellurium reagent in the high oxidation state needed to carry out the alkane functionalization reaction.

For instance, the alkylselenium or alkyltellurium C—H bond activation reaction product can be used to prepare amine derivatives of the starting alkanes or heteroalkanes, by contact of the C—H bond activation reaction product with a nitrogen-containing reagent, such as hydrazine, hydroxylamine, ammonia, ammonia, a primary or secondary amine, or an equivalent. The hydrazine or hydroxylamine reagents can be unsubstituted or can be substituted, e.g., with alkyl or aryl groups, or the like. The reaction of the organoselenium or organotellurium C—H bond activation reaction product with the nitrogen-containing reagent can be

TABLE 1

| | | | | | | | | |
|---|---|---|---|---|---|---|---|---|
| Oxidant | Conc. (M) | Solvent | Hydrocarbon | T (° C.) | Time (hr) | Products (% of total) | Analysis | Yield (based on oxidant) |
| Te(OH)$_6$ | 0.25 | TFA$_2$O-HTFA | MeH | 180 | 3 | "Te—Me" 100% | $^1$H-NMR Used $^{13}$CH$_4$ | >90% |
| H$_2$SeO$_4$ | 0.25 | TFA$_2$O-HTFA | MeH | 180 | 3 | MeTFA (10%), "Se—Me" (13%) other 77% | $^1$H-NMR | <10% |
| H$_2$SeO$_4$ | 0.25 | TFA$_2$O-HTFA | EtH | 180 | 3 | EtTFA (82%), EG(TFA)$_2$ (2%), CH$_3$CH(TFA)$_2$ (15%) | $^1$H-NMR | 23% |

Conversions of Unactivated Hydrocarbons with Iodine, Selenium, and Tellurium Reagents carried out in situ, or preferably can be carried out on a separated product stream, e.g., following a liquid-liquid extraction. The selenium or tellurium can be recovered and recycled by an oxidative step, and the amine derivative of the starting alkane can be recovered and further purified, further reacted, or both.

For instance, the alkylselenium or alkyltellurium C—H bond activation reaction product can be converted to an organotin (stannane) compound by reaction of the initial reaction product with a stannylation reagent, such as a stannous salt in the presence of an oxidant. Organotin compounds are known as versatile synthetic intermediates in a variety of reactions; see additional cited documents below.

In another embodiments, the alkylselenium or alkyltellurium C—H bond activation reaction product can be treated with a sulfur-containing reagent, such as $S_8$, or such as an alkylthiol, to provide a thiolated alkane. The organosulfur product obtained can be a thiol or a disulfide, or can be a thioether. Such compounds can be further converted to sulfoxides and sulfones by oxidation of the sulfur atom.

In further embodiments, the alkylselenium or alkyltellurium C—H bond activation reaction product can be further processed to provide a carboxamido derivative corresponding to the starting alkane; for instance, the alkylselenium or alkyltellurium reaction product can undergo reaction with a formylation reagent such as formaldehyde and an amine, such as in the presence of an oxidant, to yield a homologated derivative of the starting alkane with a pendant carboxamido group, wherein an additional carbon atom has been added to the molecule.

The alkylselenium or alkyltellurium C—H bond activation reaction product can undergo a subsequent reaction with a phosphine to provide a phosphinylated alkane corresponding to the starting material. Use of a trisubstituted phosphine can provide a phosphonium salt, while use of a mono- or disubstituted phosphine can provide the analogous phosphine derivative.

The alkylselenium or alkyltellurium C—H bond activation reaction product can be caused to undergo an elimination reaction, yielding an alkene, by treatment with a very weak base such as acetate or trifluoroacetate. The alkene can then be epoxidized, converted to a glycol, and the like.

Carbonylation of the alkylselenium or alkyltellurium C—H bond activation reaction product, such as with carbon monoxide, can provide an acyl compound that is a homolog of the starting alkane, having added an additional carbon atom. The acyl compound obtained, e.g., an aldehyde, carboxylic acid, or carboxamide, depending upon reaction conditions, can undergo further transformations, such as are well-known in the art.

The alkylselenium or alkyltellurium C—H bond activation reaction product can undergo a halogenation reaction to provide a halocarbon derivative of the starting alkane substrate, such as by the use of a halide and an oxidant such as $O_2$.

For more extensive details, the documents cited below outline some of the chemical transformations available to the alkylselenium or alkyltellurium reaction products obtained by practice of the present methods.

DOCUMENTS CITED

A. Krief, L. Hevesi, Organoselenium Chemistry I. Functional Group Transformations., Springer, Berlin, 1988 ISBN 3-540-18629-8.

S. Patai, Z. Rappoport (Eds.), The Chemistry of Organic Selenium and Tellurium Compounds, John. Wiley and Sons, Chichester, Vol. 1, 1986 ISBN 0-471-90425-2.

Paulmier, C. Selenium Reagents and Intermediates in Organic Synthesis; Baldwin, J. E., Ed.; Pergamon Books Ltd.: New York, 1986 ISBN 0-08-032484-3.

Freudendahl, Diana M.; Santoro, Stefano; Shahzad, Sohail A.; Santi, Claudio; Wirth, Thomas (2009). "Green Chemistry with Selenium Reagents: Development of Efficient Catalytic Reactions". Angewandte Chemie International Edition 48 (45): 8409-11, 2009.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A process for the conversion of an alkane or a heteroalkane, wherein the alkane or heteroalkane comprises at least one $sp^3$-hybridized carbon atom, to a corresponding alkylselenium or alkyltellurium compound comprising
   (a) contacting the alkane or heteroalkane and a soft oxidizing electrophile comprising Se(VI) or Te(VI), in an acidic medium, optionally further comprising an aprotic medium; to form the corresponding alkylselenium or alkyltellurium compound and optionally
   (b) separating the respective alkylselenium or alkyltellurium compound.

2. The process of claim 1, further comprising a step of regeneration of the soft oxidizing electrophile by contacting a Se- or Te-containing electrophile reduction product of the soft oxidizing electrophile and the alkane or heteroalkane with an oxidant under conditions suitable to regenerate the soft oxidizing electrophile comprising Se(VI) or Te(VI).

3. The process of claim 1, wherein the alkane is methane, ethane, or propane, or any mixture thereof.

4. The process of claim 1, wherein the acidic medium is free of a superacid.

5. The process of claim 2, wherein the regenerating oxidant comprises any of molecular oxygen, hydrogen peroxide, chlorine, nitric acid, or ozone.

6. The process of claim 2, wherein the regenerating oxidant consists essentially of hydrogen peroxide.

7. The process of claim 1, wherein the acidic medium consists essentially of trifluoroacetic acid, acetic acid, or a mixture thereof.

8. The process of claim 1, wherein the acidic medium further comprises an aprotic medium, comprising an anhydrous, poorly nucleophilic, polar liquid.

9. The process of claim 8, wherein the aprotic medium is liquid sulfur dioxide, trifluoroethanol, tetrachloroethane, or dichloromethane, or a mixture thereof.

10. The process of claim 1, wherein (i) the soft oxidizing electrophile comprising Se(VI) or Te(VI) (ii) the electrophile reduction product thereof, or (iii) both, are immobilized on a solid support contained within a reactor.

11. The process of claim 1, wherein the alkane or the heteroalkane and the soft oxidizing electrophile comprising Se(VI) or Te(VI) in an acidic medium are contacted in a reactor for a first period of time, followed by a second period of time in which the electrophile reduction product is contacted with an oxidant to regenerate the soft oxidizing electrophile.

12. The process of claim 1, wherein the process is carried out in a two reactor circulating liquid phase system, wherein the reaction of the alkane or the heteroalkane and the soft oxidizing electrophile is carried out in a first reactor, and the step of oxidatively regenerating the separated electrophile reduction product to the soft oxidizing electrophile is carried out in a second reactor.

13. The process of claim 1 further comprising a step of contacting the alkylselenium or alkyltellurium compound and a hydrazine, a hydroxylamine, or an amine, to provide an amine corresponding to the alkane or heteroalkane.

14. The process of claim 1 further comprising a step of contacting the alkylselenium or alkyltellurium compound and a stannous salt in the presence of an oxidant to provide an organotin compound corresponding to the alkane or heteroalkane.

15. The process of claim 1 further comprising a step of contacting the alkylselenium or alkyltellurium compound and a sulfur-containing reagent, to provide a thiolated alkane or heteroalkane.

16. The process of claim 1 further comprising a step of contacting the alkylselenium or alkyltellurium compound and formaldehyde and an amine, in the presence of an oxidant, to yield a homologated derivative of the starting alkane or heteroalkane with a carboxamido group.

17. The process of claim 1 further comprising a step of contacting the alkylselenium or alkyltellurium compound and a phosphine to provide a phosphinylated alkane or heteroalkane corresponding to the starting material.

18. The process of claim 1 further comprising a step of contacting the alkylselenium or alkyltellurium compound and a very weak base, such as acetate or trifluoroacetate, to provide an alkene.

19. The process of claim 1 further comprising a step of contacting the alkylselenium or alkyltellurium compound and carbon monoxide, to provide an acyl compound.

20. The process of claim 1 further comprising a step of contacting the alkylselenium or alkyltellurium compound and a halide in the presence of an oxidant to provide a halocarbon derivative of the starting alkane or heteroalkane substrate.

21. The process of claim 1, wherein the alkylselenium or alkyltellurium compound is separated.

* * * * *

UNITED STATES PATENT AND TRADEMARK OFFICE
CERTIFICATE OF CORRECTION

| | |
|---|---|
| PATENT NO. | : 9,505,714 B2 |
| APPLICATION NO. | : 14/910275 |
| DATED | : November 29, 2016 |
| INVENTOR(S) | : Periana et al. |

Page 1 of 1

It is certified that error appears in the above-identified patent and that said Letters Patent is hereby corrected as shown below:

In the Specification

Column 1, Lines 14-18, the paragraph STATEMENT OF GOVERNMENT SUPPORT should be changed to:
-- STATEMENT OF GOVERNMENT LICENSE RIGHTS
This invention was made with government support under grant number DE-PS02-08ER15944 awarded by the United States Department of Energy. The government has certain rights in the invention. --

Signed and Sealed this
Fifth Day of May, 2020

Andrei Iancu
*Director of the United States Patent and Trademark Office*